(12) United States Patent
Yokokubo

(10) Patent No.: US 11,238,974 B2
(45) Date of Patent: Feb. 1, 2022

(54) INFORMATION PROCESSING APPARATUS, INFORMATION PROCESSING METHOD, AND STORAGE MEDIUM STORING PROGRAM

(71) Applicant: CANON KABUSHIKI KAISHA, Tokyo (JP)

(72) Inventor: Anna Yokokubo, Tokyo (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 737 days.

(21) Appl. No.: 14/704,053

(22) Filed: May 5, 2015

(65) Prior Publication Data

US 2015/0324521 A1   Nov. 12, 2015

(30) Foreign Application Priority Data

May 9, 2014 (JP) ................................. 2014-097862

(51) Int. Cl.
*G16H 30/00* (2018.01)
*G16H 30/20* (2018.01)

(52) U.S. Cl.
CPC ............. *G16H 30/20* (2018.01); *G16H 30/00* (2018.01)

(58) Field of Classification Search
CPC .... G06Q 50/22; G06Q 50/24; G06F 19/3443; A61B 6/465; A61B 6/463
USPC .......................................... 705/2–3; 382/128
See application file for complete search history.

(56) References Cited

U.S. PATENT DOCUMENTS

| 5,581,460 | A | * | 12/1996 | Kotake | G06F 19/3487 |
|---|---|---|---|---|---|
| | | | | | 705/3 |
| 7,069,506 | B2 | * | 6/2006 | Rosenholtz | G06F 16/9577 |
| | | | | | 715/273 |
| 2002/0078090 | A1 | * | 6/2002 | Hwang | G06F 17/30707 |
| | | | | | 715/201 |
| 2003/0189602 | A1 | * | 10/2003 | Dalton | G06F 3/0483 |
| | | | | | 715/830 |
| 2004/0101176 | A1 | * | 5/2004 | Mendonca | G06T 7/0012 |
| | | | | | 382/128 |
| 2005/0119914 | A1 | * | 6/2005 | Batch | A61B 5/411 |
| | | | | | 705/2 |
| 2006/0274928 | A1 | * | 12/2006 | Collins | A61B 6/00 |
| | | | | | 382/132 |

(Continued)

FOREIGN PATENT DOCUMENTS

| CN | 101347355 A | 1/2009 |
|---|---|---|
| CN | 102844783 A | 12/2012 |

(Continued)

*Primary Examiner* — John P Go
(74) *Attorney, Agent, or Firm* — Canon U.S.A., Inc. IP Division

(57) ABSTRACT

An information processing apparatus includes an acquisition unit configured to acquire patient's medical information, an extraction unit configured to extract a part of the medical information as material candidates for a reduced medical image, a selection unit configured to assign priorities to a plurality of the extracted material candidates, and, based on the priorities, select materials to be used for generation of the reduced medical image out of a plurality of the material candidates, and a generation unit configured to generate the reduced medical image based on a plurality of the selected materials.

19 Claims, 8 Drawing Sheets

(56) References Cited

U.S. PATENT DOCUMENTS

| | | | | |
|---|---|---|---|---|
| 2006/0277073 | A1* | 12/2006 | Heilbrunn | G16H 15/00 705/3 |
| 2007/0143714 | A1* | 6/2007 | Barbieri | G06F 16/54 715/861 |
| 2007/0237378 | A1* | 10/2007 | Reiner | G06Q 10/06 382/128 |
| 2008/0059245 | A1* | 3/2008 | Sakaida | G06F 19/321 705/3 |
| 2010/0114597 | A1* | 5/2010 | Shreiber | G16H 10/60 705/2 |
| 2010/0274584 | A1* | 10/2010 | Kim | G06F 19/322 705/3 |
| 2011/0002515 | A1* | 1/2011 | Futami | G16H 10/60 382/128 |
| 2011/0075913 | A1* | 3/2011 | Moriya | G16H 30/40 382/132 |
| 2011/0137132 | A1* | 6/2011 | Gustafson | A61B 5/7264 600/300 |
| 2011/0137169 | A1* | 6/2011 | Akaki | G16H 30/20 600/443 |
| 2011/0184760 | A1* | 7/2011 | Shen | G06Q 10/10 705/3 |
| 2012/0096014 | A1* | 4/2012 | Davids | G06Q 10/10 707/749 |
| 2013/0120454 | A1* | 5/2013 | Shechtman | G06T 3/0012 345/635 |
| 2013/0152020 | A1* | 6/2013 | Nishiyama | A61B 1/00009 715/835 |
| 2013/0188857 | A1* | 7/2013 | Yoshihara | G01N 33/574 382/133 |
| 2014/0108053 | A1* | 4/2014 | Akaki | A61B 8/00 705/3 |
| 2015/0149180 | A1* | 5/2015 | Lee | G10L 13/00 704/260 |

FOREIGN PATENT DOCUMENTS

| | | | |
|---|---|---|---|
| CN | 102984417 A | 3/2013 | |
| JP | H07-168845 A | 7/1995 | |
| JP | 2002-259006 A | 9/2002 | |
| JP | 2005-056390 A | 3/2005 | |
| JP | 2005-287632 A | 10/2005 | |
| JP | 2007-066016 A | 3/2007 | |
| JP | 2012-247879 A | 12/2012 | |
| JP | 2013-228800 A | 11/2013 | |
| KR | 10-2014-0046900 A | 4/2014 | |
| WO | WO-2006115517 A2 * | 11/2006 | G06F 16/40 |
| WO | 2009/110310 A1 | 9/2009 | |
| WO | 2011/033769 A1 | 3/2011 | |
| WO | 2013/137280 A1 | 9/2013 | |
| WO | 2013/137281 A1 | 9/2013 | |

* cited by examiner

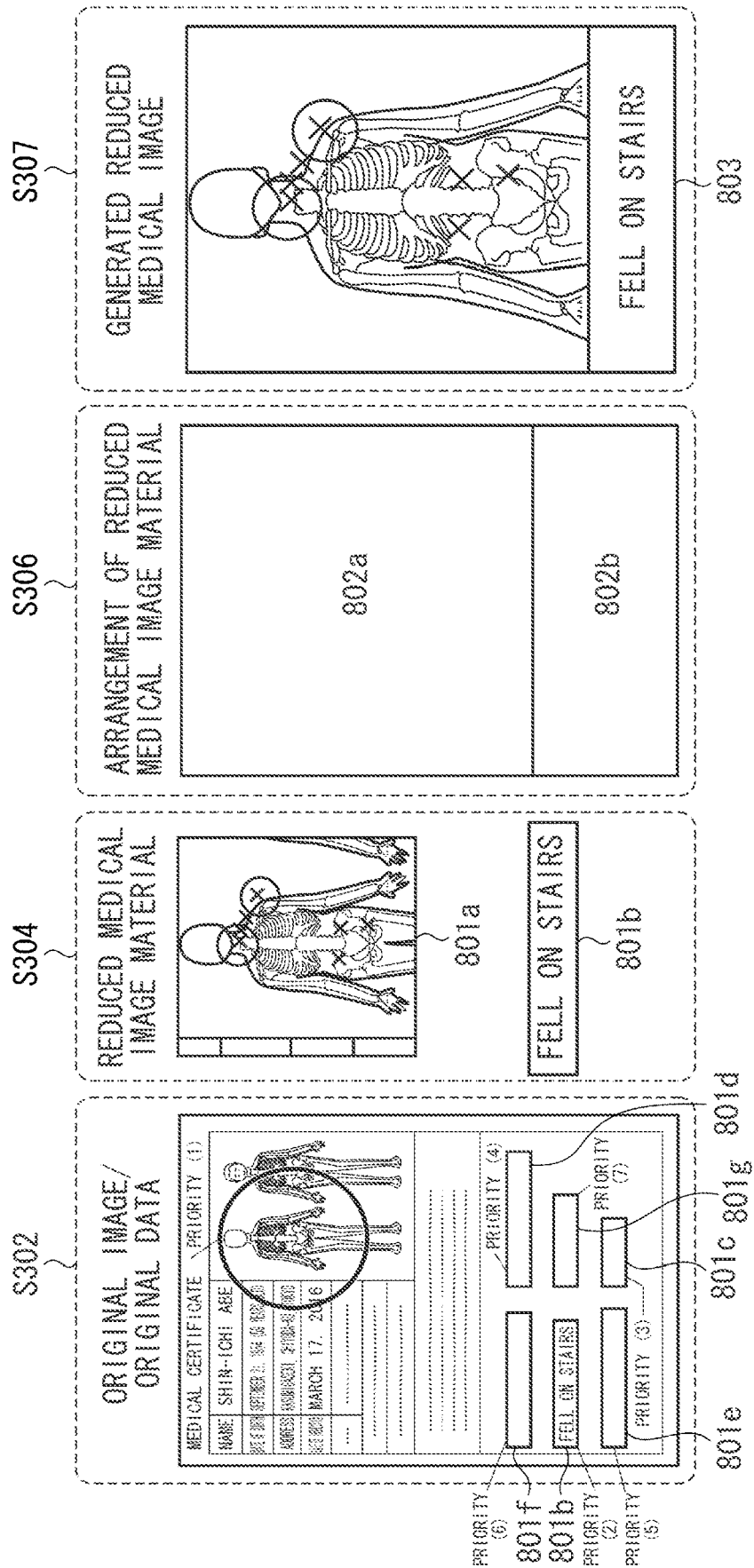

INFORMATION PROCESSING APPARATUS, INFORMATION PROCESSING METHOD, AND STORAGE MEDIUM STORING PROGRAM

BACKGROUND OF THE INVENTION

Field of the Invention

The present invention generally relates to an information processing, in particular it relates to an information processing apparatus, an information processing method, and a computer-readable storage medium storing a program, which are applicable to patient's medical information.

Description of the Related Art

In recent years, with the increase in the use of medical information systems, such as a Hospital Information System (HIS), a Picture Archiving and Communication System (PACS), and a Radiology Information System (RIS), an increasing number of medical images and documents have been digitized.

Accordingly, medical images including X-ray images, computerized tomography (CT) images, magnetic resonance imaging (MRI) images or other images generated by other medical imaging modalities, and medical documents including medical records have been digitized, resulting in an enormous amount of patient information to be dealt with.

As a system for integrating medical images and medical documents and enabling browsing of patient information, a medical information overview system is currently being introduced to medical facilities such as hospitals.

The medical information overview system has been introduced to information terminals operated by doctors and other medical workers. The medical information overview system enables browsing and confirming a patient's medical images and medical documents on monitors connected to information terminals to take a comprehensive overview of a patient's medical information.

More specifically, the medical information overview system displays a desirable reduced medical image in a screen having a matrix structure formed of a time series axis and an axis of a medical image apparatus (modality apparatus).

However, in the medical information overview system which displays wide variety and a number of reduced medical images, it is difficult and burdensome for a user to extract desired information since an enormous number of reduced medical images are displayed. Generally, in the medical information overview system, reduced medical images can only be displayed one by one because of a limited region for displaying reduced medical images.

To improve the above situation, methods for extracting and displaying images useable as reduced medical images are being considered.

A technique discussed in Japanese Patent Application Laid-Open No. 7-168845 determines a timing of generating a reduced medical image from a large amount of original images based on a configuration of a reduced medical image management mechanism, enabling efficient generation of a reduced medical image. One of representative images (key images) extracted from a plurality of images provided by the modality apparatus is used to generate a target reduced medical image.

As a general method for extracting key images, a certain technique uses images at a central slice of a group of captured images. However, if key images are used for the purpose of browsing such a small image as a reduced medical image, degradation in visual image quality and in visibility arises.

A technique discussed in Japanese Patent Application Laid-Open No. 2005-56390 clips images from respective regions inside one image, and uses a part of the clipped images to generate a reduced image.

However, the technique discussed in Japanese Patent Application Laid-Open No. 2005-56390 does not generate a reduced medical image showing browsability desired by the user.

SUMMARY OF THE INVENTION

According to an aspect of the present invention, an information processing apparatus includes an acquisition unit configured to acquire patient's medical information, an extraction unit configured to extract a part of the medical information as material candidates for a reduced medical image, a selection unit configured to assign priorities to a plurality of the extracted material candidates, and, based on the priorities, select materials to be used for generation of the reduced medical image out of the plurality of the material candidates, and a generation unit configured to generate the medical reduced image based on a plurality of the selected materials.

Further features of the present invention will become apparent from the following description of exemplary embodiments with reference to the attached drawings.

BRIEF DESCRIPTION OF THE DRAWINGS

FIG. 8 illustrates automatic generation of a reduced medical image for a medical interview sheet.

DESCRIPTION OF THE EMBODIMENTS

Exemplary embodiments of the present invention will be described below with reference to the accompanying drawings.

Figure 1:
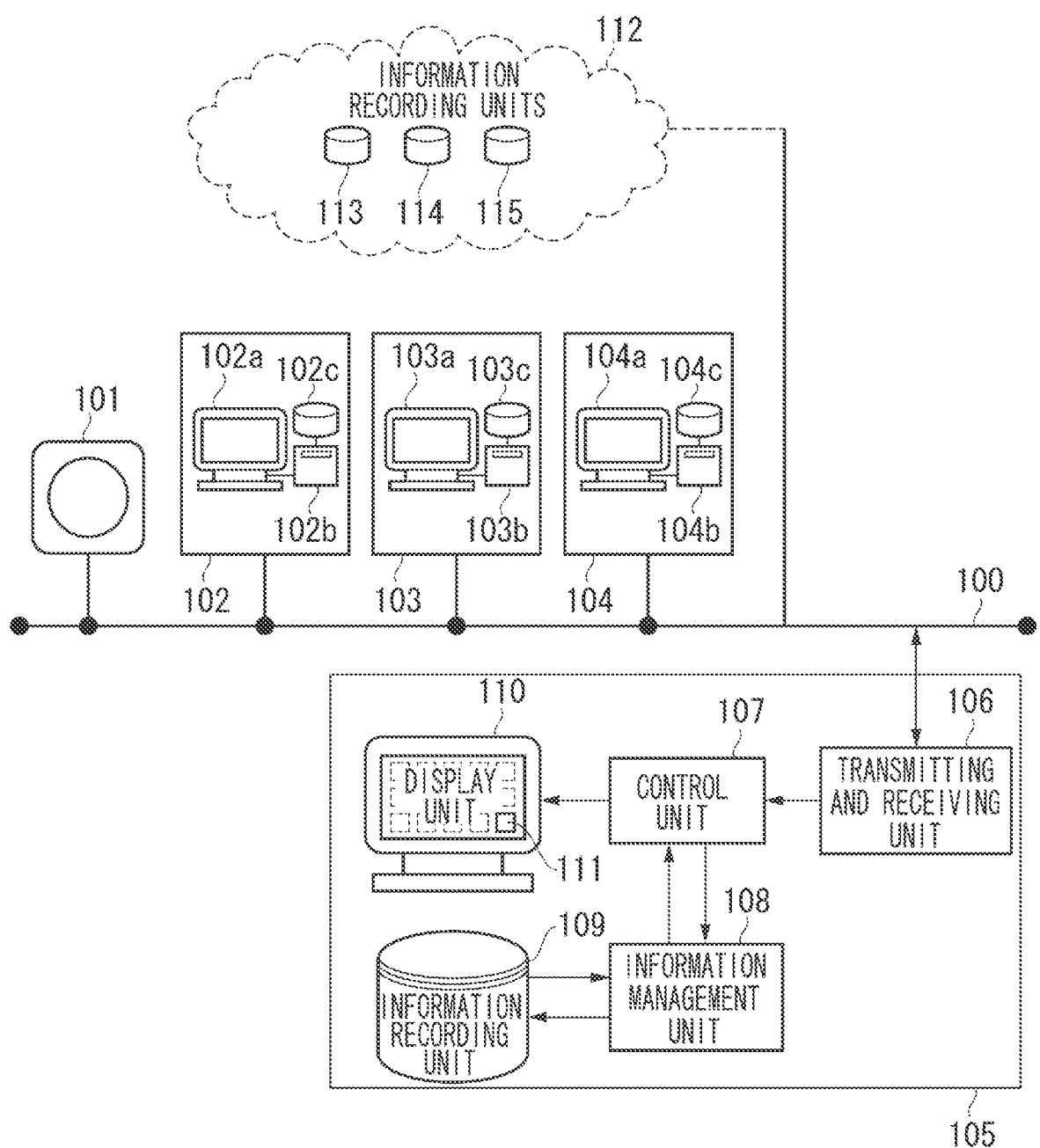
FIG. 1 schematically illustrates an example of a configuration of a medical information overview system.

A first exemplary embodiment will be described below. FIG. 1 schematically illustrates an example of a configuration of a medical information overview system including a reduced medical image processing apparatus.

Referring to FIG. 1, a modality apparatus 101, an intra-hospital system (including an HIS 102, an RIS 103, a PACS 104, and a medical reduced image processing apparatus 105), and an information recording unit (a cloud 112) are connected to a network 100 to enable communicating with each other.

The modality apparatus 101 captures images of a subject's region to be inspected to generate two- or three-dimensional image data of the region. The medical information overview system includes an apparatus for adding supplementary information prescribed by the Digital Imaging and Communication in Medicine (DICOM) standard to the image data, and outputting resultant image information. The image data may include text information which accompanies images. Captured medical images are transmitted to the HIS 102, the RIS 103, and the PACS 104 via the network 100.

The HIS 102 includes an HIS information display unit 102a, an HIS information control unit 102b, and an HIS information recording unit 102c. HIS information may also be stored in an HIS information recording unit 113 in the cloud 112 in addition to the HIS information recording unit 102c.

The HIS information recording unit 102c and the HIS information recording unit 113 in the cloud 112 store patient's personal information, including name, gender, age, height, weight, nationality, and so on. As patient's medical information, the HIS information recording unit 102c and the HIS information recording unit 113 further store overall intra-hospital information regarding patients, including patient's medical conditions, a medical history, inspection results, diagnostic results, radiogram interpretation reports, medical images, and so on.

The HIS information control unit 102b may be implemented in the HIS 102 as hardware or as software. When the HIS information control unit 102b is implemented as software, the HIS 102 includes at least a central processing unit (CPU) and a memory as hardware. When the CPU executes processing based on a program stored in the memory, the HIS information control unit 102b functions as software.

The RIS 103 includes an RIS information display unit 103a, an RIS information control unit 103b, and an RIS information recording unit 103c. RIS information may also be stored in the RIS information recording unit 114 in the cloud 112 in addition to the RIS information recording unit 103c.

The RIS information recording unit 114 and the RIS information recording unit 112b in the cloud 112 store inspection results obtained by non-radiation apparatuses such as an ultrasonic apparatus, an endoscope, and a fundus camera, medical treatment records and overall information regarding inspection reservation.

The RIS information control unit 103b may be implemented in the RIS 103 as hardware or as software. When the RIS information control unit 103b is implemented as software, the RIS 103 includes at least a CPU and a memory as hardware. When the CPU executes processing based on a program stored in the memory, the RIS information control unit 103b functions as software.

The PACS 104 includes a PACS information display unit 104a, a PACS information control unit 104b, and a PACS information recording unit 104c. PACS information may be stored in the PACS information recording unit 115 in the cloud 112 in addition to the PACS information recording unit 104c.

The PACS information recording unit 104c and the PACS information recording unit 115 in the cloud 112 register medical images and accompanying information. As the accompanying information, the PACS information recording unit 104c and the PACS information recording unit 112c store overall information regarding medical images, such as an image identifier (ID) for identifying each individual image, a patient's ID for identifying a subject, the date and time of inspection, and so on. When a radiogram interpretation report is generated, the PACS information recording unit 104c and the PACS information recording unit 112c further store overall information regarding radiogram interpretation such as an x-ray analyst name, radiogram interpretation images, findings, and so on.

The PACS information control unit 104b may be implemented in the PACS 104 as hardware or as software. When the PACS information control unit 104b is implemented as software, the PACS 104 includes at least a CPU and a memory as hardware. When the CPU executes processing based on a program stored in the memory, the PACS information control unit 104b functions as software.

The reduced medical image processing apparatus 105 includes a transmitting and receiving unit 106, a control unit 107, an information management unit 108, an information recording unit 109, and a display unit 110.

The display unit 110 displays reduced medical images 111 in a list form. The display format of the reduced medical images 111 is not limited to the example. The display unit 110 displays reduced medical images 111 in a list form to facilitate confirmation of patient information.

The transmitting and receiving unit 106, the control unit 107, and the information management unit 108 may be implemented in the medical reduced image processing apparatus 105 as hardware or as software. When the transmitting and receiving unit 106, the control unit 107, and the information management unit 108 are implemented as software, the reduced medical image processing apparatus 105 includes at least a CPU and a memory as hardware. When the CPU executes processing based on a program stored in the memory, the transmitting and receiving unit 106, the control unit 107, and the information management unit 108 function as software.

The cloud 112 is a system to which a plurality of computers is connected via the network 100. The cloud 112 provides other apparatuses with web services (services related to information storage in the present exemplary embodiment) via the network 100. The information recording unit 109 may be included in the cloud 112.

Figure 2:
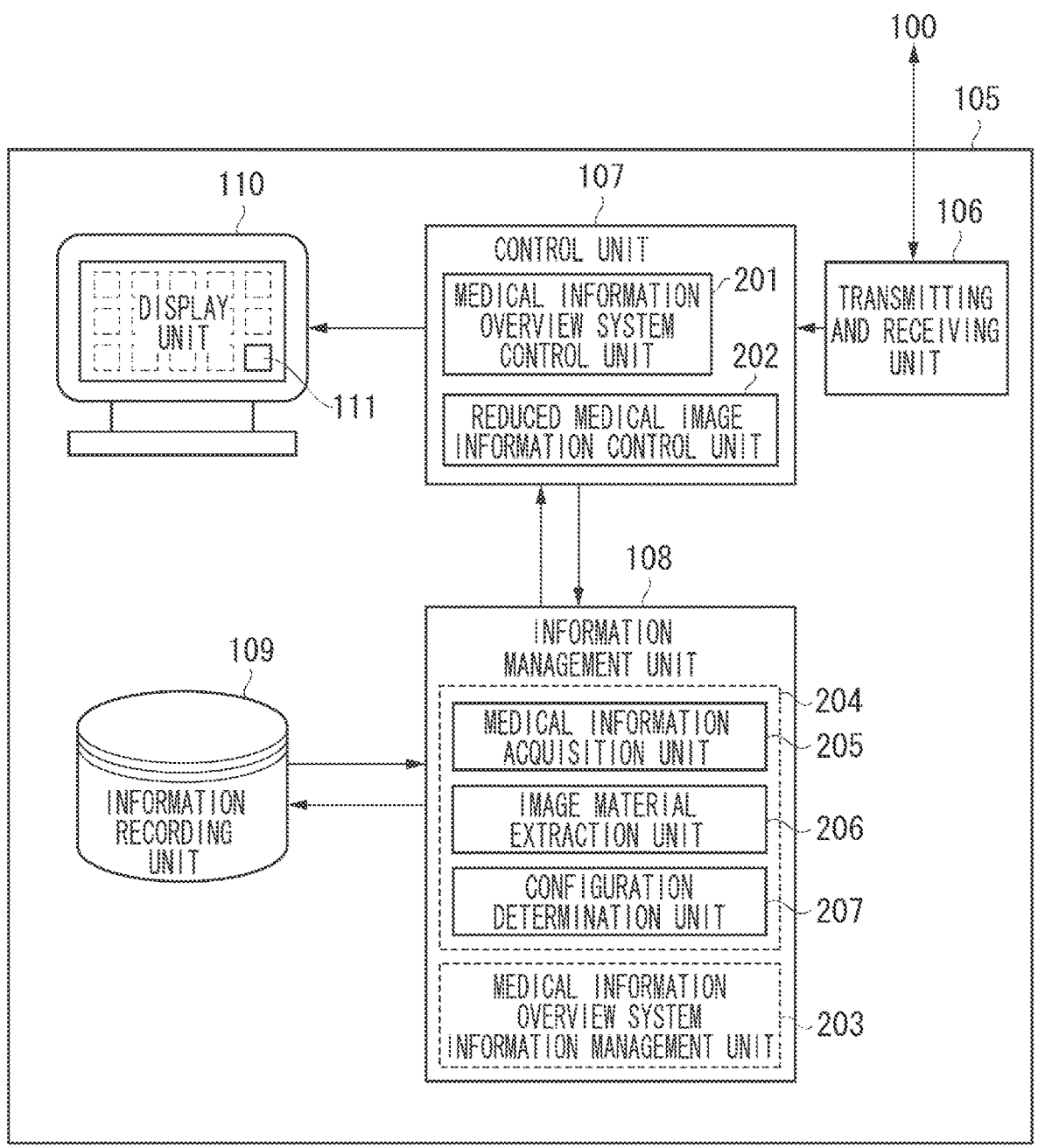
FIG. 2 illustrates an example of a functional configuration of a reduced medical image processing apparatus.

FIG. 2 illustrates an example of a functional configuration of the reduced medical image processing apparatus 105.

Referring to FIG. 2, the reduced medical image processing apparatus 105 includes the transmitting and receiving unit 106, the control unit 107, the information management unit 108, the information recording unit 109, and the display unit 110.

The control unit 107 includes a medical information overview system control unit 201 and a reduced medical image information control unit 202. The medical information overview system control unit 201 arranges patient information included in the HIS 102, the RIS 103, and the PACS 104 with a specified method, for example, in time series via the transmitting and receiving unit 106 connected to the network 100, and displays the arranged information on the display unit 110. The reduced medical image information control unit 202 collectively controls generated medical reduced images.

The information management unit 108 includes an overview system information management unit 203 for medical information and a reduced medical image information management unit 204. The reduced medical image information management unit 204 includes a medical information acquisition unit 205, an image material extraction unit 206, and a configuration determination unit 207. The medical information acquisition unit 205 acquires patient's medical information included in the HIS 102, the RIS 103, and the PACS 104 via the transmitting and receiving unit 106 connected to the network 100. The image material extraction unit 206 extracts a part of a plurality of medical images and medical documents based on the patient's medical information. The configuration determination unit 207 determines a configuration of a reduced medical image by using image materials.

Figure 3:
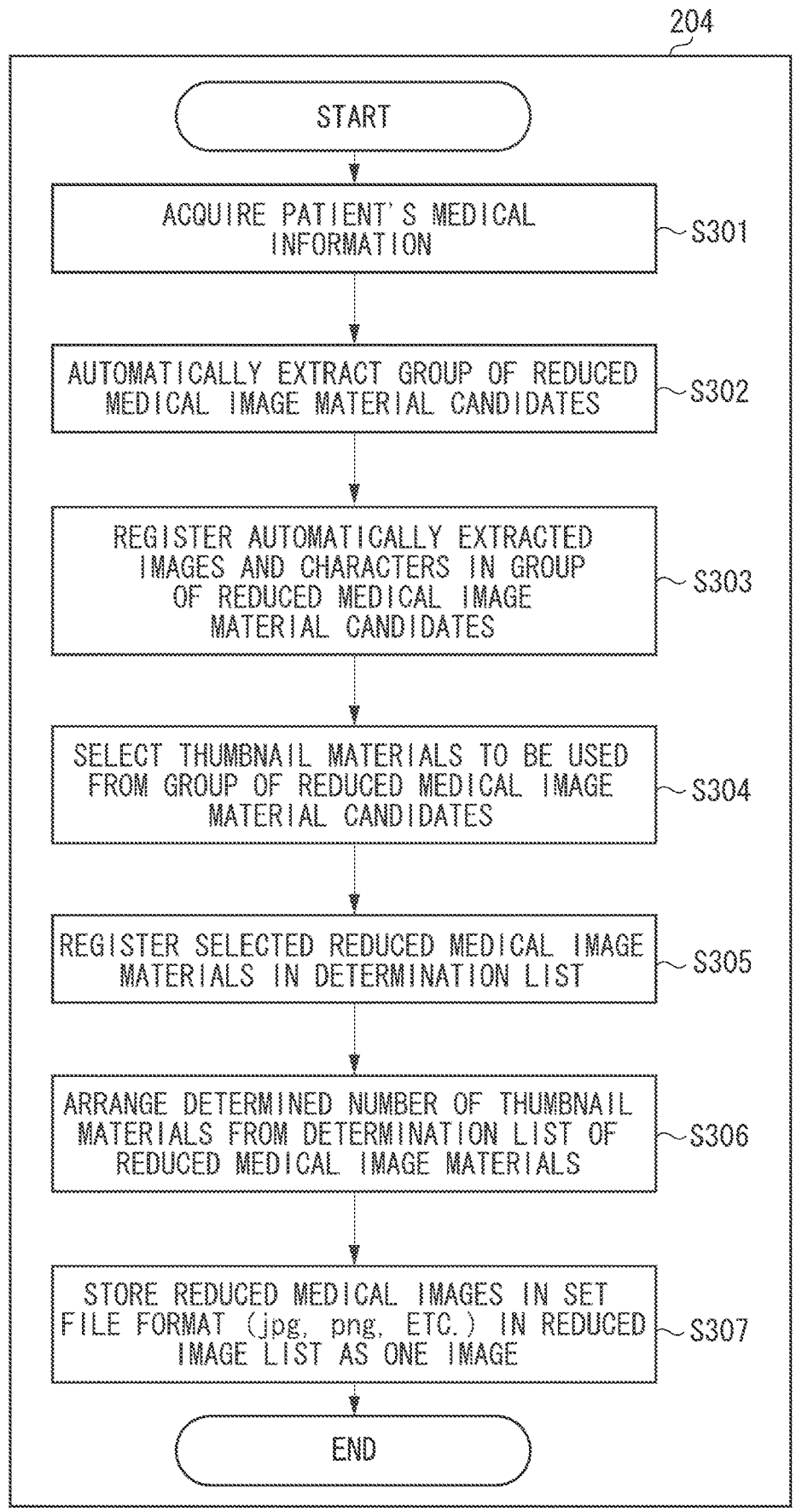
FIG. 3 is a flowchart illustrating information processing executed by the reduced medical image processing apparatus.

FIG. 3 is a flowchart illustrating information processing performed by the medical reduced image processing apparatus 105.

Referring to FIG. 3, the reduced medical image information management unit 204 performs the following processing.

In step S301, the medical information acquisition unit 205 acquires the patient's medical information included in the HIS 102, the RIS 103, and the PACS 104 via the network 100.

In step S302, based on the acquired medical information, the image material extraction unit 206 automatically extracts a group of reduced medical image material candidates which are determined to be necessary for each clinical department or disease. Processing in step S302 will be described in detail below with reference to FIG. 4.

In step S303, the image material extraction unit 206 temporarily registers automatically extracted images and characters.

In step S304, the image material extraction unit 206 selects reduced medical image materials to be actually used, from the group of reduced medical image material candidates temporarily registered in step S303. Processing in step S304 will be described in detail below with reference to FIG. 5.

In step S305, the image material extraction unit 206 temporarily registers the reduced medical image materials selected in step S304 in a material determination list.

In step S306, the configuration determination unit 207 arranges the images and characters registered in step S305 on a reduced medical image template according to a reduced medical image size to generate a reduced medical image. Processing in step S306 will be described in detail below with reference to FIG. 6.

After completing the arrangement in step S306, in step S307, the configuration determination unit 207 stores the generated reduced medical image in a reduced medical image fixed list in an established file format (jpg, png, etc.) as one image.

A reduced medical image is generated in the above-described steps S301 to S307.

Figure 4:
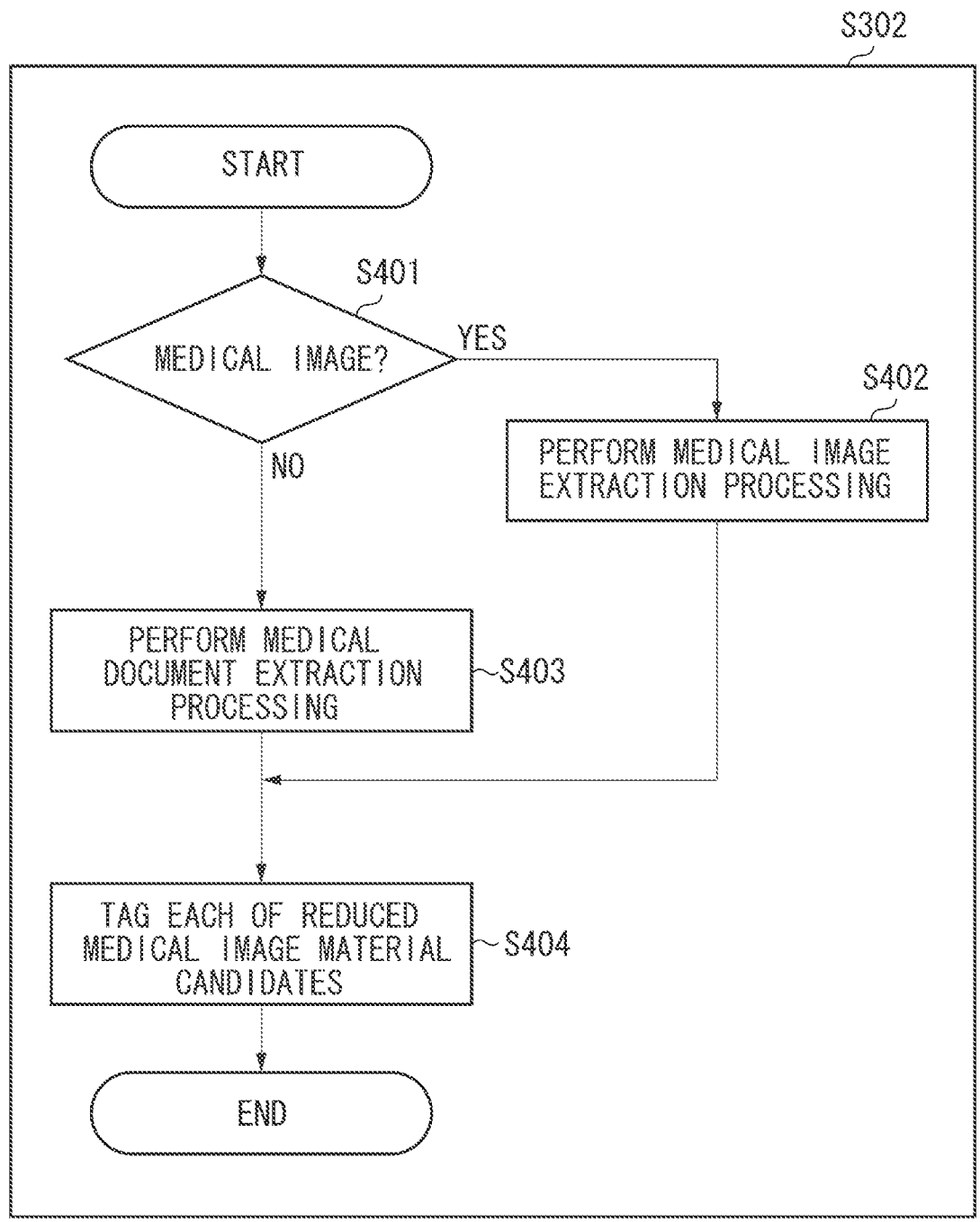
FIG. 4 is a flowchart illustrating an example of information processing in step S302.

FIG. 4 is a flowchart illustrating an example of information processing in step S302.

The patient's medical information acquired in step S301 includes radiogram interpretation reports, medical interview sheets, medical documents in a request form, as well as electronic medical charts including results of CT and X-ray image inspections, patient's SOAP, and a medical history. "S" in SOAP represents subjective data (i.e., patient's subjective symptoms), "O" in SOAP represents objective data (i.e., objective findings based on physical examinations and inspections), "A" in SOAP represents assessment (i.e., an evaluation based on S and O), and "P" in SOAP represents plan (i.e., a plan based on S, O, and A).

In step S302, the image material extraction unit 206 extracts a part of medical images or medical documents usable as reduced medical image materials from the patient's medical information acquired in step S301.

First of all, in step S401, the image material extraction unit 206 determines whether process targets are medical images based on the patient's medical information. When process targets are medical images (YES in step S401), the processing proceeds to step S402. On the other hand, when process targets are not medical images (NO in step S401), the processing proceeds to step S403.

In step S402, the image material extraction unit 206 performs medical image extraction processing to acquire a part of the above-described medical images as reduced medical image materials. Processing in step S402 will be described in detail below.

On the other hand, in step S403, the image material extraction unit 206 performs medical document extraction processing to acquire a part of the above-described medical documents as reduced medical image materials. Processing in step S403 will be described in detail below.

In step S404, the image material extraction unit 206 tags each of the acquired reduced medical image materials. For example, according to types of the acquired reduced medical image materials, the image material extraction unit 206 tags the medical reduced image materials corresponding to their types. Types include, for example, representative images (key images), a diagnostic name, and main symptoms. Types and tags are examples of attribute information.

Processing illustrated in FIG. 4 will be described in more detail below. When the patient's medical information acquired in step S301 is a CT image (YES in step S401), the processing proceeds to step S402. When the patient's medical information is only medical images, the image material extraction unit 206 determines YES in step S401. On the other hand, when the patient's medical information is not only medical images, the image material extraction unit 206 determines NO in step S401. More specifically, when the medical information includes information other than medical images, such as character strings, the image material extraction unit 206 determines NO in step S401, even if the patient's medical information includes images.

In step S402, the image material extraction unit 206 extracts representative images (key images) from CT images as reduced medical image material candidates. More specifically, the image material extraction unit 206 identifies a key image from CT images by using an image recognition technique, and extracts a rectangular region including a mark in the identified key image as one of reduced medical image material candidates. This is because a mark such as an arrow is likely used to describe a lesion area in the key image.

When the patient's medical information acquired in step S301 is scan data of a medical interview sheet (NO in step S401), then in step S403, the image material extraction unit 206 extracts description portions about main symptoms, a time when main symptoms appeared, and a human body diagram, from the scan data of the medical interview sheet, as reduced medical image material candidates. A general medical interview sheet is standardized for each hospital or each clinical department. For example, the image material extraction unit 206 identifies a hospital and a clinical department based on predetermined regions of the medical interview sheet, acquires information about a medical interview sheet template standardized for each hospital or each clinical department, and acquires relevant data based on region information defined by the template. The image material extraction unit 206 may identify a hospital and a clinical department based on a medical interview sheet by using an image recognition technique.

When the patient's medical information acquired in step S301 is an electronic medical chart (NO in step S401), then in step S403, the image material extraction unit 206 extracts description portions about SOAP, a diagnostic name, and items to be noted from the electronic medical chart. In the case of an electronic medical chart, position information of description portions about SOAP, the diagnostic name, and the items to be noted is preset. Therefore, for example, based on the preset position information, the image material extraction unit 206 extracts description portions about SOAP, the diagnostic name, and items to be noted from relevant positions of the electronic medical chart.

In the processing described above with reference to FIG. 4, the image material extraction unit 206 extracts a part of medical images or medical documents usable as reduced medical image materials from the patient's medical information. However, the image material extraction unit 206 may extract a part of both medical images and medical documents as reduced medical image material candidates.

In the processing described above with reference to FIG. 4, the image material extraction unit 206 automatically extracts reduced medical image material candidates. However, the image material extraction unit 206 may make an inquiry to an operator of the reduced medical image processing apparatus 105, and, based on a selection operation by the operator, extract an image and a character string at the selected portion as reduced medical image material candidates.

Figure 5:
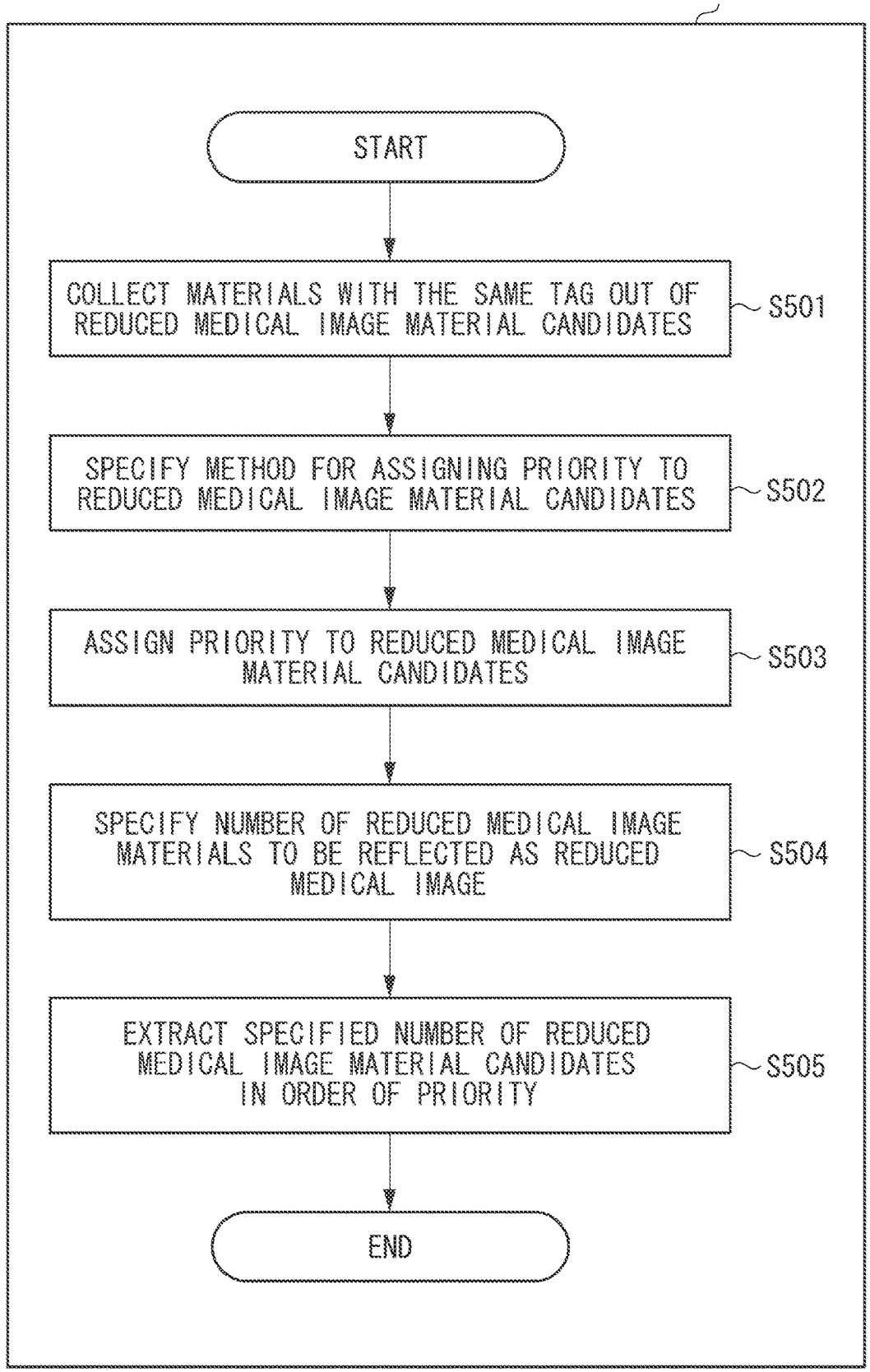
FIG. 5 is a flowchart illustrating an example of information processing in step S304.

FIG. 5 is a flowchart illustrating an example of information processing in step S304.

When a medical reduced image is generated, reduced medical image materials which can be reflected in a reduced medical image form are limited due to the size of the form. Accordingly, it is necessary to determine reduced medical image materials to be used for the reduced medical image.

Therefore, to select reduced medical image materials to be actually used from the group of reduced medical image material candidates temporarily registered in step S303, the image material extraction unit 206 determines priorities of reduced medical image materials and the number of materials to be arranged in the target reduced medical image.

In step S501, based on the tag specified in step S404, the image material extraction unit 206 collects reduced medical image material candidates tagged with an identical tag name. The image material extraction unit 206 determines priorities of reduced medical image material candidates tagged with an identical tag name, as illustrated below.

The image material extraction unit 206 prompts the operator of the reduced medical image processing apparatus 105 to select a priority assignment method (a rule for assigning priorities) via a screen. In step S502, the image material extraction unit 206 acquires the priority assignment method selected by the operator via the screen, and specifies the priority assignment method. The image material extraction unit 206 may automatically specify a priority assignment method according to the patient's medical information acquired in step S301.

In step S503, the image material extraction unit 206 assigns priorities to reduced medical image material candidates based on the specified priorities.

Processing in step S503 is described below using a more concrete example.

When automatically generating a reduced medical image for a radiogram interpretation report, higher priorities are assigned to a key image, a diagnostic name, and a region where a disease is inferred by an x-ray analyst (hereinafter referred to as a disease-inferred region). In particular, visual information is required to make an image function as a reduced medical image. Therefore, the image material extraction unit 206 assigns the first priority to the key image, and the second priority to the diagnostic name and the disease-inferred region. In step S503, with respect to reduced medical image materials showing an equal priority such as descriptions of the diagnostic name or the disease-inferred region, the image material extraction unit 206 assigns higher priorities to materials which are determined to be on the higher level by a diagnostic support technique. When automatically assigning priorities, setting information is recorded, for example, in the information record unit 109. This setting information indicates what is assigned the highest priority depending on what kind of reduced medical image is automatically generated. The image material extraction unit 206 assigns priorities based on this setting information.

When automatically generating a reduced medical image for a medical interview sheet, priorities to be assigned differ for each clinical department. In the case of internal medicine, the main symptoms and the time when main symptoms appeared are important. Therefore, the image material extraction unit 206 assigns the first priority to the main symptoms, and the second priority to the time when main symptoms appeared. In the case of orthopedic surgery and dermatology, main symptoms are often added to the human body diagram described in a medical interview sheet. Therefore, in step S503, the image material extraction unit 206 assigns the first priority to the human body diagram, and the second priority to the main symptoms.

When automatically generating a reduced medical image for an electronic medical chart, in step S503, the image material extraction unit 206 assigns the first priority to SOAP and a diagnostic name, and the second priority to items to be noted.

When automatically generating a reduced medical image for a test result, in step S503, the image material extraction unit 206 assigns the first priority to the image of a lesion area in the case of medical images, and assigns the first priority to abnormal values or numerical values requiring follow-up observation in the case of numerical values of a test result.

When priorities of reduced medical image material candidates have been determined, in step S504, the image material extraction unit 206 specifies the number of reduced medical image materials to be taken as the reduced medical image. The image material extraction unit 206 determines the number of medical reduced image materials based on the size of the reduced medical image (the format of the medical reduced image). More specifically, when automatically determining the number of materials based on the size of the reduced medical image, the image material extraction unit 206 categorizes the format size of the reduced medical image into 3 (large, medium, and small) to (extra-large, large, medium, small, and extra-small) different sizes, and determines the number of materials according to the format size of the reduced medical image. The image material extraction unit 206 determines the number of materials for the reduced medical image categorized as "small" to be on the order of 1 to 2, the number of materials for the medical reduced image categorized as "medium" to be on the order of 2 to 4, and the number of materials for the medical reduced image categorized as "large" to be on the order of 3 to 5. The categorization method is not limited thereto.

As described above, the image material extraction unit 206 may automatically determine the number of reduced medical image materials based on the format size of the reduced medical image, and may specify the number of materials according to an operation by the operator via a screen. However, because of the characteristics of a reduced medical image, if a plurality of images is inserted into the format of the reduced medical image, the visibility is degraded. Therefore, it is desirable to limit the number of divisions depending on the format size of the reduced medical image. Therefore, also when specifying the number of materials according to an operation by the operator, the image material extraction unit 206 may limit the number of materials which can be specified, depending on the format size of the reduced medical image.

In step S505, in order of priorities assigned in step S503, the image material extraction unit 206 extracts the number of reduced medical image materials specified in step S504 from the reduced medical image material candidates.

Figure 6:
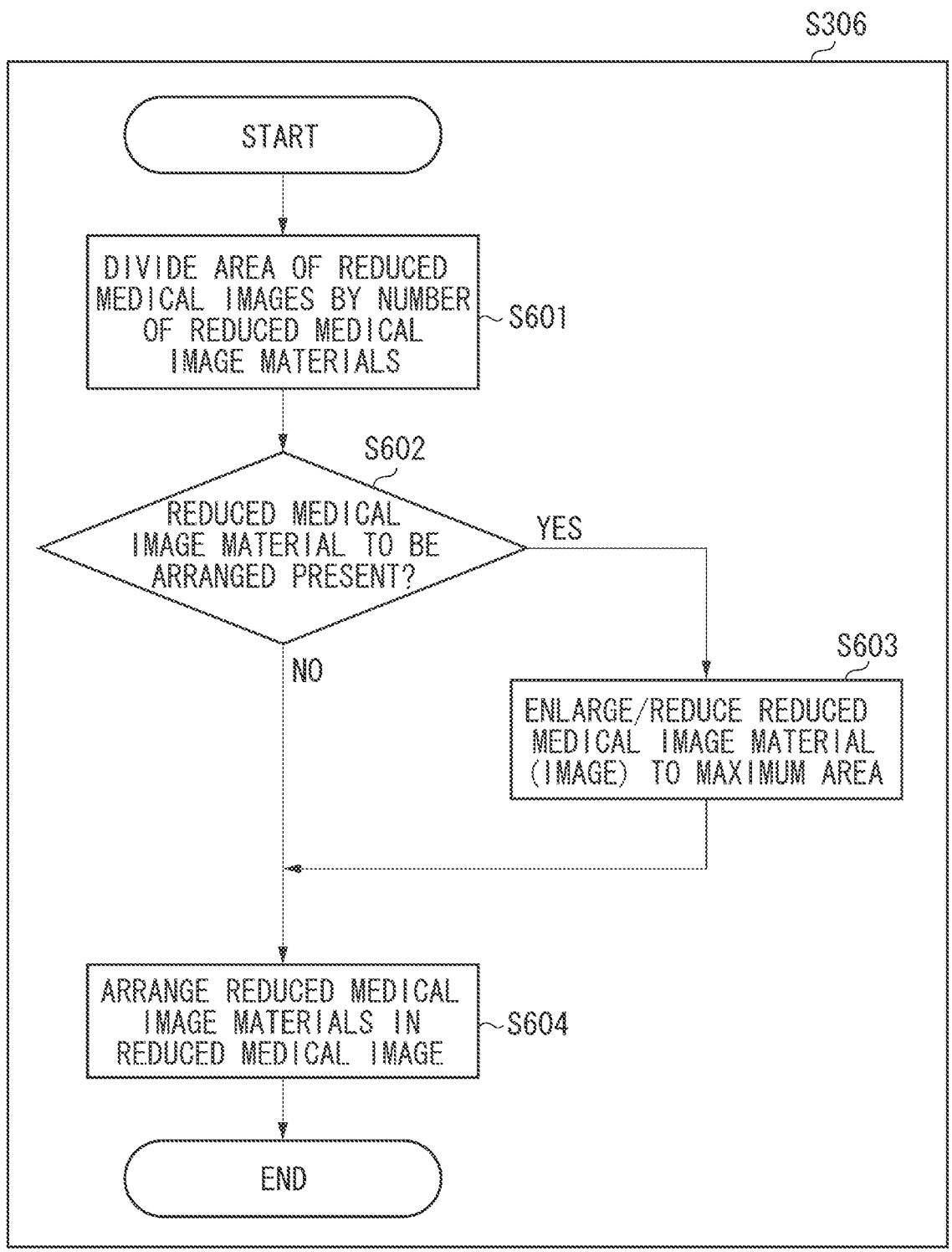
FIG. 6 is a flowchart illustrating an example of information processing in step S306.

FIG. 6 is a flowchart illustrating an example of information processing in step S306.

In step S601, the configuration determination unit 207 divides the area of the format of the reduced medical image by the number of materials (the number of reduced medical image materials) specified in step S504 illustrated in FIG. 5.

In step S602, the configuration determination unit 207 determines whether there is a reduced medical image material to be arranged in the reduced medical image. When there is a reduced medical image material to be arranged (YES in step S602), the processing proceeds to step S603. On the other hand, when there is no reduced medical image material to be arranged (NO in step S602), the processing proceeds to step S604. The configuration determination unit 207 determines that there is still a reduced medical image material to be arranged if the processing illustrated in FIG. 6 is not completed for any reduced medical image material among the number of the materials extracted in step S505.

In step S603, the configuration determination unit 207 enlarges or reduces the reduced medical image material showing the highest priority, of medical reduced image materials which have not completed the processing illustrated in FIG. 6, to cover the maximum area allowable in the format of the reduced medical image. In step S604, the configuration determination unit 207 repeats the processing in steps S602 and S603 until there remains no reduced medical image materials to be arranged, and then arranges reduced medical image materials in the format of the reduced medical image. A region where reduced medical image materials are to be arranged is predetermined in the format of the reduced medical image (described below). In the order of priorities of reduced medical image materials, the configuration determination unit 207 arranges the reduced medical image materials in a region of the above-described format of the reduced medical image which has a large area.

Upon completion of arrangement, the configuration determination unit 207 stores the reduced medical image in a set image format, as illustrated in step S307 illustrated in FIG. 3.

Figure 7:
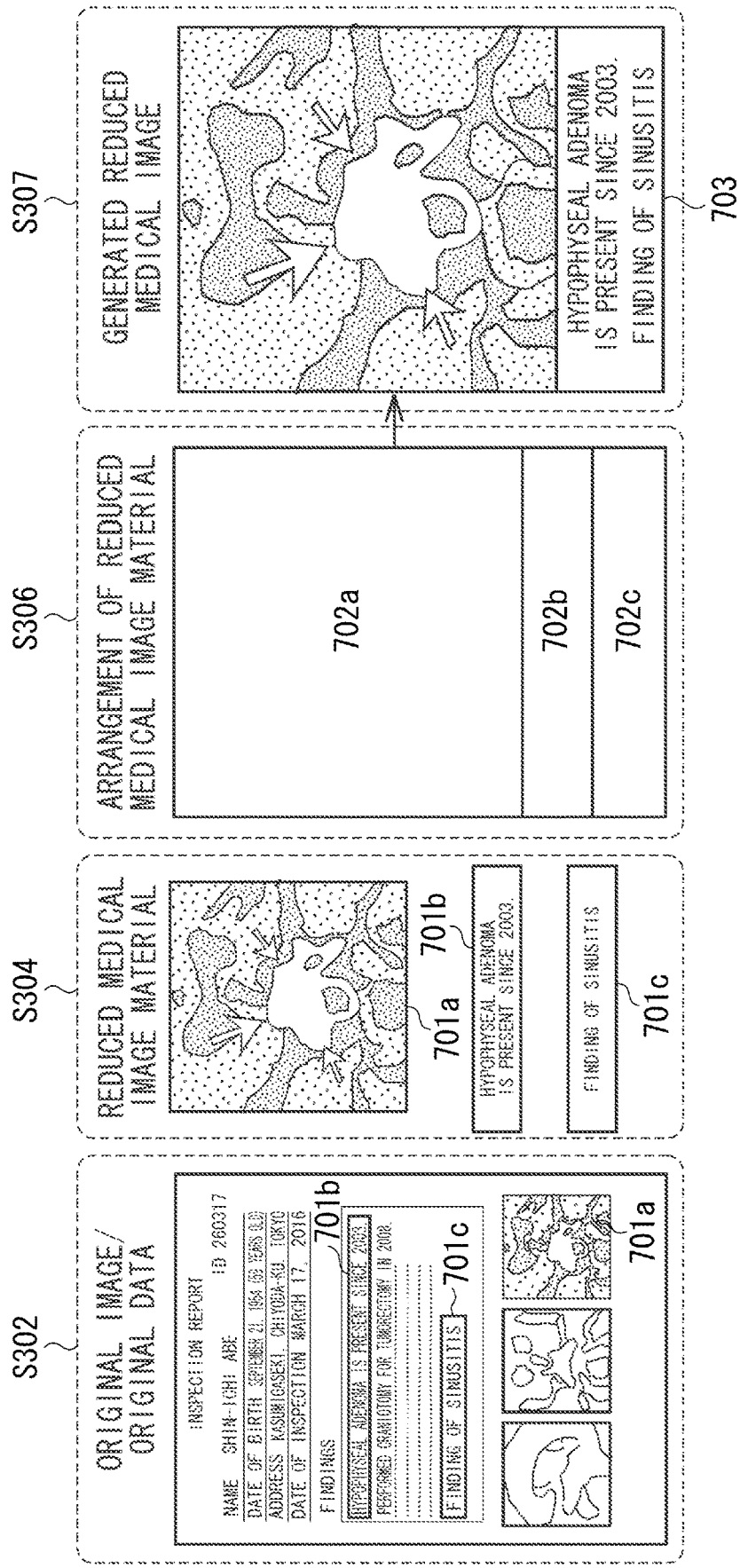
FIG. 7 illustrates automatic generation of a medical reduced image for a radiogram interpretation report.

FIG. 7 illustrates automatic generation of a reduced medical image for a radiogram interpretation report.

In step S301 illustrated in FIG. 3, the medical information acquisition unit 205 acquires a patient's radiogram interpretation report. In step S302 illustrated in FIG. 3, the image material extraction unit 206 extracts a group of reduced medical image material candidates. In the case of a radiogram interpretation report, a key image 701a, a time when main symptoms appeared 701b, and a diagnostic finding/name 701c are extracted as a group of reduced medical image material candidates.

In step S304 illustrated in FIG. 3, the image material extraction unit 206 assigns priorities to reduced medical image material candidates. In the case of a radiogram interpretation report, for example, the image material extraction unit 206 assigns the highest priority to the key image 701a, assigns the second highest priority to the time when main symptoms appeared 701b, and assigns the third highest priority to the diagnostic finding/name 701c.

Since the number of reduced medical image materials is specified to be 3 as illustrated in FIG. 7, reduced medical image materials are sequentially arranged in step S306 illustrated in FIG. 3 in the order of priorities so that the reduced medical image material showing the highest priority occupies the largest area ratio. More specifically, reduced medical image materials are arranged so that a reduced medical image material assigned a higher priority occupies a larger ratio of the medical reduced image. Referring to FIG. 7, the area of the key image 701a is enlarged or reduced to occupy a maximum area (a region 702a). The time when main symptoms appeared 701b and the diagnostic finding/name 701c are enlarged or reduced to occupy the maximum area within a range excluding the region 702a, the time when main symptoms appeared 701b is arranged in a region 702b, and the diagnostic finding/name 701c is arranged in a region 702c. Processing performed by the configuration determination unit 207 to adjust each material to occupy the maximum area is not limited to enlargement and reduction. The processing may be performed, for example, by changing a shape.

When all of reduced medical image materials are arranged, in step S307 illustrated in FIG. 3, a reduced medical image 703 for a radiogram interpretation report is generated and then stored in a set file format, as illustrated in FIG. 7.

FIG. 8 illustrates automatic generation of a reduced medical image for a medical interview sheet.

In step S301 illustrated in FIG. 3, the medical information acquisition unit 205 acquires a patient's medical interview sheet. In step S302 illustrated in FIG. 3, the image material extraction unit 206 extracts a group of reduced medical image material candidates. In the case of a medical interview sheet, a human body diagram 801a, a cause of main symptoms 801b, a disease region 801c, a degree of pain 801d, supplementary information about a cause of main symptoms 801e, a time when the main symptoms appeared 801f, and supplementary information about the time when main symptoms appeared 801g are extracted as a group of reduced medical image material candidates. In step S304 illustrated in FIG. 3, the image material extraction unit 206 assigns priorities to the extracted materials. In the case of a patient's medical interview sheet, for example, the image material extraction unit 206 assigns the highest priority to the human body diagram 801a, and assigns the second highest priority to the cause of main symptoms 801b. Likewise, the image material extraction unit 206 assigns priorities to reduced medical image material candidates, as illustrated in FIG. 8.

Since the specified number of reduced medical image materials is 2 as illustrated in FIG. 8, reduced medical image materials are sequentially arranged in step S306 illustrated in FIG. 3 in the order of priorities so that the reduced medical image material showing the highest priority occupies the largest area. Referring to FIG. 8, the area of the human body diagram 801a is enlarged or reduced to occupy a maximum area (a region 802a). The cause of main symptoms 801b is enlarged or reduced to occupy the maximum area within a range excluding the region 802a (a region 802b). Processing performed by the configuration determination unit 207 to adjust each material to occupy the maximum area is not limited to enlargement and reduction. The processing may be performed by changing a shape or changing color (highlighting) relevant parts of the reduced medical image material showing the highest priority.

When all of the reduced medical image materials are arranged, in step S307 illustrated in FIG. 3, a reduced medical image 803 for a medical interview sheet is generated and then stored in a set file format, as illustrated in FIG. 8 (right most frame).

In the examples described above with reference to FIGS. 7 and 8 as more specific examples for automatically generating a reduced medical image, a reduced medical image is automatically generated from a radiogram interpretation report and from a medical interview sheet, respectively. However, original data for the reduced medical image is not limited thereto.

A second exemplary embodiment will be described below. The medical information overview system has to be capable of instantaneously confirming past and present situations of a patient. Therefore, the medical information overview system may display (perform display control) on the display unit 110 a plurality of the reduced medical images according to the first exemplary embodiment and utilize them to support medical examination of a patient.

In addition, an information processing apparatus (computer) may display a reduced medical image and, which is utilized as explanatory material for patients, for example, material for obtaining informed consent.

A generated reduced medical image may be used in printed form, or be reused by other systems.

According to the above-described exemplary embodiments, it is possible to generate an advanced browser for reduced medical image. If the advanced browser is displayed for reduced medical image on a medical information overview system, medical workers can quickly recognize patient's situations. Meanwhile, a reduced image refers to, for example, an icon.

Other Embodiments

Embodiments of the present invention can also be realized by a computer of a system or apparatus that reads out and executes computer executable instructions recorded on a storage medium (e.g., non-transitory computer-readable storage medium) to perform the functions of one or more of the above-described embodiment(s) of the present invention, and by a method performed by the computer of the system or apparatus by, for example, reading out and executing the computer executable instructions from the storage medium to perform the functions of one or more of the above-described embodiment(s). The computer may comprise one or more of a central processing unit (CPU), micro processing unit (MPU), or other circuitry, and may include a network of separate computers or separate computer processors. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2014-097862, filed May 9, 2014, which is hereby incorporated by reference herein in its entirety.

What is claimed is:

1. An information processing apparatus comprising:
a memory storing a program; and
one or more processors which, by executing the program, function as:
an acquisition unit configured to acquire patient's medical information including medical documents and medical images;
a determination unit configured to determine the number of materials to be used for generation of a thumbnail;
an extraction unit configured to extract a part of the medical documents and the medical images as the material for the thumbnail based on the patient's medical information, wherein the extraction unit extracts a string of characters from the medical documents as a first material and extracts a representative medical image including a lesion area from the medical images as a second material in the case where the determination unit determines the number of materials to be at least two;
an assignment unit configured to assign a plurality of priorities to the first material and the second material, wherein a low priority is assigned to the first material and a high priority is assigned to the second material; and
a generation unit configured to generate the thumbnail including the string of characters and the representative medical image by combining the first material and the second material, wherein the generation unit generates the thumbnail so that an area of the second material is larger than an area of the first material, in accordance with the assigned priorities.

2. The information processing apparatus according to claim 1, wherein, the first material is at least one of a diagnostic finding and a diagnostic name.

3. The information processing apparatus according to claim 1, wherein the second material is a part of the medical image.

4. The information processing apparatus according to claim 1, wherein the generation unit generates a plurality of thumbnails each of which includes different materials, and further comprising:
a display control unit configured to control a display unit to display the plurality of thumbnails for instantaneously confirming past and present situations of a patient.

5. The information processing apparatus according to claim 1, wherein the determination unit is configured to determine the number of materials to be used for generation of the thumbnail based on a size of the thumbnail.

6. The information processing apparatus according to claim 1, wherein the medical document is a radiogram interpretation report.

7. The information processing apparatus according to claim 1, wherein the extraction unit extracts a region including a mark out of the medical images for the representative medical image.

8. The information processing apparatus according to claim 1, wherein, according to information about a clinical department or disease included in the medical information, the extraction unit extracts the part of the medical information including the medical document and the medical images.

9. An information apparatus comprising:
a memory storing a program; and
one or more processors which, by executing the program, function as:
an acquisition unit configured to acquire patient's medical information including medical documents and medical images;
a determination unit configured to determine the number of materials to be used for generation of a thumbnail;
an extraction unit configured to preferentially extract the medical images based on the number of materials determined by the determination unit as the material for the thumbnail based on the patient's medical information, wherein the extraction unit extracts a string of characters from the medical documents as a first material and extracts a representative medical image including a lesion area from the medical images as a second material in the case where the determination unit determines the number of materials to be at least two;
a generation unit configured to generate the thumbnail including the string of characters and the representative medical image by combining the first material and the second material, wherein the generation unit generates the thumbnail so that an area of the second material is larger than an area of the first material, wherein the thumbnail is divided based on the number of materials determined by the determination unit;
a display control unit configured to control a display unit to display a plurality of thumbnails including the string of characters and the representative medical image generated by the generation unit in the time series.

10. An information processing method executed by an information processing apparatus, the method comprising:
acquiring patient's medical information including medical documents and medical images;
determining the number of materials to be used for generation of a thumbnail;
preferentially extracting the medical images based on the determined number of materials as the material for the thumbnail based on the patient's medical information, wherein a string of characters from the medical documents as a first material and a representative medical image including a lesion area from the medical images as a second material are extracted in the case where the number of materials to be at least two materials is determined;
generating the thumbnail including the string of characters and the representative medical image by combining the first material and the second material, wherein the thumbnail is generated so that an area of the second material is larger than an area of the first material, wherein the thumbnail is divided based on the number of materials determined by the determination unit;
a display control unit configured to control a display unit to display a plurality of thumbnails including the string of characters and the generated representative medical image.

11. The information processing apparatus according to claim 9, wherein the first material is at least one of a diagnostic finding and a diagnostic name.

12. The information processing apparatus according to claim 9, wherein the second material is a part of the medical image.

13. The information processing apparatus according to claim 9, wherein the generation unit generates a plurality of thumbnails each of which includes different materials, and further comprising:
a display control unit configured to control a display unit to display the plurality of thumbnails for instantaneously confirming past and present situations of a patient.

14. The information processing apparatus according to claim 9, wherein the determination unit is configured to determine the number of materials to be used for generation of the thumbnail based on a size of the thumbnail.

15. The information processing apparatus according to claim 9, wherein the medical document is a radiogram interpretation report.

16. The information processing apparatus according to claim 9, wherein the thumbnail including the string of characters and the representation medical image is stored in a set file format in a storage medium.

17. The information processing apparatus according to claim 9, wherein each of the medical documents and the medical images is tagged with a tag name.

18. The information processing apparatus according to claim 17, wherein the extraction unit extracts the medical documents and the medical images tagged with an identical tag name.

19. The information processing apparatus according to claim 1, wherein, according to information about a clinical department or disease included in the medical information, the extraction unit extracts the part of the medical information including the medical document and the medical images.

* * * * *